United States Patent [19]

LLorente Agudo et al.

[11] 4,351,903

[45] Sep. 28, 1982

[54] PROCESS FOR OBTAINING GLUCOSE-ISOMERASE

[75] Inventors: Nieves LLorente Agudo; Maria F. Elia Miguel; Maria A. Arangurén Escobar; Eulalia Pares Olivet; José M. Fernández Garvajosa, all of Madrid, Spain

[73] Assignee: Compania Espanola de Petroleos, S.A., Spain

[21] Appl. No.: 202,766

[22] Filed: Oct. 31, 1980

[30] Foreign Application Priority Data

Oct. 31, 1979 [ES] Spain .................................... 485.580

[51] Int. Cl.³ .............................................. C12N 9/92
[52] U.S. Cl. ..................................... 435/234; 435/886
[58] Field of Search ................................. 435/234, 233

[56] References Cited

U.S. PATENT DOCUMENTS

| 4,255,521 | 3/1981 | Hirohara et al. | 435/234 |
| 4,256,838 | 3/1981 | Jackson et al. | 435/234 |
| 4,291,123 | 9/1981 | Degen et al. | 435/94 |

Primary Examiner—Lionel M. Shapiro
Attorney, Agent, or Firm—Wenderoth, Lind & Ponack

[57] ABSTRACT

There is provided a process for producing glucose-isomerase in high yield by culturing under aerobic conditions, the strain *Streptomyces griseoflavus* (NCIB 11542).

11 Claims, No Drawings

PROCESS FOR OBTAINING GLUCOSE-ISOMERASE

PURPOSE OF THE INVENTION

This invention describes a process for the preparation of glucose-isomerase from a strain of the genus Streptomyces, as well as a culture medium in which the strain is capable of producing the enzyme in continuous culture.

TECHNICAL-ECONOMICAL JUSTIFICATION

The demand for fructose has increased in the latest years, since because of its sweetening power, low calories and profitability, it can compete with the sugar commonly used, sucrose.

It is known that the enzyme glucose-isomerase can be used for the conversion (epimerization) of glucose (dextrose) into fructose (levulose). Different micro-organisms, capable of producing the enzyme glucose-isomerase have been described, including bacteria of the genders Bacillus, Escherichia, Aerobacter, Lactobacillus, Arthrobacter, and Pseudomonas. Other micro-organisms capable of achieving said transformation are some species of the Order Actinomycetales, such as *Actinoplanes missouriensis, Streptomyces phaeochromogenes, Streptomyces albus, Streptomyces flavovirans.*

This patent discloses the production of the enzyme glucose-isomerase by a strain of the species *Streptomyces griseoflavus.*

This species, isolated from soil samples, presents as its greatest advantage a high specific speed of growth, which implies a lower risk of contamination during its culture in the fermenter. At the same time, it permits its culture at high speeds of dilution, which leads towards a production of enzyme comparable to that of other micro-organisms of a higher specific activity.

The present invention also comprises a description of the species, a method for the production of the enzyme glucose-isomerase in culture media which contain, among others, soy flour, tryptone and xylans. The latter modification was introduced with the purpose of lowering the cost of the culture medium, due to the high price of xylose.

DESCRIPTION OF THE INVENTION

A strain of the species *Streptomyces griseoflavus*, isolated from a soil sample by the present inventors, has been studied.

The taxonomic characteristics of the strain *Streptomyces griseoflavus* A-40 (National Collection of Industrial Bacteria, Aberdeen Scotland, NCIB-11542) are as follows:

1. Morphologic properties:
   a. Abundant aerial grey mycelium.
   b. Morphology of the aerial mycelium: Chain of spores, with the shape of a spiral. Spores with a thorny surface.
   c. Melanoyd pigment: Negative.
2. Culture properties:
   Aspect after ten days at 25° C.

TABLE I

| Medium | Aerial Mycelium | Mycelium Substrate | Pigment Diffusible |
|---|---|---|---|
| Malt-yeast agar | Dark grey | Brown | |
| Salts-starch agar | Somewhat grey | Pale yellow | — |
| Glucose-asparagine agar | No aerial hyphes | Pale yellow | — |
| Glyceral-asparagine agar | No aerial hyphes | Pale yellow | — |
| Oatmeal agar | grey | Yellowish orange | — |
| Water sucrose nitrate | No aerial hyphes | Pale yellow | — |
| Agar tyrosine | Somewhat pale grey | Pale yellow | — |
| Nutrient agar | Pale grey | Pale yellow | — |
| Agar peptone iron | No aerial hyphes | Pale yellow | — |
| Agar melanoyd pigment | No aerial hyphes | Antenned | |
| Temperature of growth: | It grows between 25° C. and 37° C. | | |
| pH of culture: | It grows between 4.5 and 9 | | |
| Demand of oxygen: | Aerobic | | |

3. Physiological and Biochemical Properties:
   a. Hydrolyzes gelatine, casein and starch
   b. Action in litmus milk: weak
   c. The use of the following carbonated compounds, as the only source of carbon in Pridham and Gottlieb's medium, is positive in the cases of glucose, xylose, arabinose, ramnose, fructose, galactose, mannitol, inositol and sucrose, while neither raffinose nor salicin are used.

Said strain of *Streptomyces griseoflavus* A-40 has been made grow in aerobic conditions in a culture medium containing a source of carbon, a source of nitrogen and inorganic salts. As the source of carbon, several sugars have been added, the best results being obtained by the addition of xylose to the medium as the substance to induce the production of glucose-isomerase. In some cases, the xylose has been totally or partially substituted by xylans. Other sources of carbon that can be used are: lactic serum, milk, molasses, sucrose, lactose, maltose, glucose, fructose and glycerol.

The sources of Nitrogen used in the culture medium were: Triptone, soy flour, yeast extract, ammonium salt, meat extract, liquid of macerated corn, and their mixtures and combinations.

All the culture media present the following composition as far as mineral salts are concerned:

TABLE II

| | |
|---|---|
| $(NH_4)_2SO_4$ | 0.3% p/v |
| $MgSO_4.7 H_2O$ | 0.025% p/v |
| $Na_2HPO_4$ | 0.2% p/v |
| $KH_2PO_4$ | 0.02% p/v |
| Solution of traces | 1% v/v |
| Antifoam | 0.1% v/v |

The composition of the solution of traces is the following:

TABLE III

| | |
|---|---|
| $MgSO_4.7 H_2O$ | 0.6% p/v |
| $CaCl_2.2 H_2O$ | $1.5 \times 10^{-3}$% p/v |
| $FeSO_4.7 H_2O$ | $2.8 \times 10^{-3}$% p/v |
| $ZnSO_4.7 H_2O$ | $1.4 \times 10^{-2}$% p/v |
| $CuSO_4.5 H_2O$ | $2.5 \times 10^{-3}$% p/v |
| $NaMoO_4.2 H_2O$ | $2.4 \times 10^{-2}$% p/v |
| $CoCl_2.2 H_2O$ | $2.4 \times 10^{-3}$% p/v |

TABLE III-continued

| | |
|---|---|
| $MnSO_4.H_2O$ | $8.4 \times 10^{-3}\%$ p/v |

The conditions of inoculum and culture for all the examples are the following:

A. Preparation of the inoculum:

The inoculum was prepared from a culture in agar xylose of *Streptomyces griseoflavus* A-40, by inoculating an erlenmeyer of 250 ml. containing 100 ml. of sterile medium. The composition of the medium for cuture was modified according to the type of medium used for the continuous culture. The medium was sterilized after adjusting the pH at 7.2. The erlenmeyer was inoculated with 5% (volume/volume) of inoculum, and incubated for 17-24 hours at 34° C. in an orbital incubator at 150-200 r.p.m. After 3-4 successive passes in the same medium, a cellular suspension representing 10% of the total volume of the culture medium of the fermenter was used as inoculum of same.

B. Continuous culture.

For the continuous production of glucose-isomerase of *Streptomyces griseoflavus* A-40, 2- and 15-liter fermenters with aeration, agitation, pH and temperature under control have been used. The inoculation was done as described in the above paragraph. The cuture media used are described in the examples.

The conditions of culture were:

Temperature: The temperature of culture was 30°-37° C.

pH: The pH was maintained at 7-7.5 with HCl 1 N.

Aeration-agitation: Both the aeration and agitation used were variable due to the fact that the transfer of Oxygen is different in the fermenters of 2 liters and 15 liters. In the case of the 2-liters fermenter, the agitation rate was 750 r.p.m. and the aeration 1 volume/volume/minute; whereas in the 15-liters fermenter the agitation rate was 400 r.p.m. and the aeration 1 v/v/min.

Dilution speed: 12-17 hours after inoculation of fermenters with the strain *Streptomyces griseoflavus*, it was put in continuous. The speed of dilution ranged between 0.05 and 0.4 $h^{-1}$, varying according to investigation needs.

Determination of activity Glucose-Isomerase.

1. Collection of cells.

The cells are separated from the culture medium by filtering through a cellulose acetate filter with pores 0.8μ diameter. They are twice washed with imidazole buffer (see Table IV); the volume of imidazole buffer used was double the volume of culture broth filtered.

TABLE IV

| | |
|---|---|
| Imidazole | $5.10^{-2}M$ |
| $CoCl_2.6 H_2O$ | $10^{-3}M$ |
| $MgSO_4.7 H_2O$ | $10^{-2}M$ |

The washed cells are collected and resuspended in imidazole buffer, the volume thereof used being double the volume of filtered culture broth.

The resuspension of cells is homogenized in a homogenizer at room temperature, for 30 seconds.

2. Isomerization reaction.

In a test tube containing 1 ml. of the cellular suspension described above, 3 ml. of isomerization medium are added. (see Table V).

The reaction takes place at 60° C. during one hour. After this time, the reaction of isomerization is stopped by adding 1 ml. of HCl 1 N and quickly cooling to 4° C. The glucose freed in the isomerization medium is determined in an automatic glucose analyzer.

The unit of activity is defined as glucose micromoles obtained per minute for a definite amount of enzyme, under the conditions described above.

TABLE V

| | |
|---|---|
| Fructose | 45% |
| $MgSO_4.7 H_2O$ | $5.10^{-3}M$ |
| $CoCl_2.6 H_2O$ | $5.10^{-4}M$ |
| Imidazole | $5.10^{-2}M$ | pH = 7.8 at room temperature

The following examples illustrate typical aspects of the invention. It is understood, however, that they are presented with the purpose of illustrating and must not be considered as restrictive.

EXAMPLE I

This example describes in detail the results obtained in a continuous process of the strain *Streptomyces griseoflavus* A-40. This micro-organism was cultivated in a medium the mineral salts of which were described in the tables II and III above. The source of Carbon used was 0.7% of xylose, and as source of Nitrogen, 0.5% of soy flour and 0.01% of meat extract.

The concentration of soy flour was determined in prior studies, in a non-continuous process, at concentrations ranging between 0.25% and 1.5%. The best results are obtained at concentrations between 0.4 and 0.6%.

The soy is subjected to a pre-treatment at pH = 8.6 for 20 minutes at 121° C., and further filtering. The rest of the components of the medium are added to the filtrate, with the exception of the xylose. The pH is adjusted to 7.2 and is sterilized at 121° C. for 20 minutes.

Once the culture medium is at room temperature, xylose previously sterilized by filtering is added.

The culture conditions are:

pH = 7.2

Temperature = 34° C.

Agitation = 750 r.p.m.

The putting in continuous was done 17 hours after inoculation.

The results obtained are shown in TABLE VI.

TABLE VI

| Cultivation time (hours) | Speed of dilution | pH | Units/gram of complete cells |
|---|---|---|---|
| 17 | — | 7.3 | 278 |
| 23 | 0.1 | 7.11 | 406 |
| 41 | 0.1 | 7.16 | 318 |
| 48 | 0.1 | 7.14 | 263 |
| 65 | 0.2 | 7.15 | 253 |
| 68 | 0.2 | 7.18 | 287 |
| 70 | 0.2 | 7.18 | 283 |
| 143 | 0.2 | 7.17 | 276 |
| 161 | 0.2 | 7.14 | 208 |
| 167 | 0.2 | 7.10 | 222 |
| 185 | 0.2 | 7.16 | 215 |
| 191 | 0.25 | 7.15 | 270 |
| 209 | 0.3 | 7.18 | 269 |
| 215 | 0.3 | 7.14 | 253 |

The specific speed of growth, $\mu_{max}$, determined by the "wash-out" technique, was 0.732 $h^{-1}$ calculated according to the formula:

$$ln\ X_t = ln\ X_o + (\mu_{max} - D)t$$

where:

$X_o$ = initial cellular concentration (gm/l)
$X_t$ = final cellular concentration (gm/l)
D = Speed of dilution
t = Time in which the count goes from $X_o$ to $X_t$

EXAMPLE 2

In this example the strain of *Streptomyces griseoflavus* A-40 was cultivated in a medium the sources of Carbon of which were xylose and sucrose, and the sources of Nitrogen, tryptone and yeast extract, though these can be used as sources of Carbon. The mineral salts of the medium were the same as in example 1.

The culture conditions were:
pH: 7.2 to 7.5
Temperature: 34° C.
Agitation: 40 r.p.m.
Pressure: 0.05 bar.
Oxygen dissolved, no less than 20%

Table VII shows the effect of the concentration of sucrose, xylose, tryptone, yeast extract, in the production of Glucose-Isomerase by the strain *Streptomyces griseoflavus* A-40. The presence of tryptone in the culture medium besides the yeast extract, stimulates the growth of the micro-organism, as well as the production of enzyme. The sucrose not only inhibits the growth, but the production of enzyme as well.

TABLE VII

| Composition of culture medium (%) | | | | Speed Dilut. | pH | Cell. Concentration | $\mu$/g of complete cells |
|---|---|---|---|---|---|---|---|
| Sucrose | Xylose | Tryptone | Yeast Ext. | | | | |
| — | 1 | 1 | — | 0.05 | 7 | 3.07 | 410 |
| 1 | 1 | 1 | — | 0.05 | 7 | 3.38 | 334 |
| 0.5 | 0.5 | 0.5 | 0.25 | 0.18 | 7 | 5.78 | 210 |
| 0.5 | 0.5 | 1 | 0.25 | 0.18 | 7 | 6.01 | 251 |
| — | 1 | 1 | 0.5 | 0.18 | 7 | 7.40 | 347 |
| — | 1 | 1.3 | 0.85 | 0.18 | 7.5 | 9.90 | 334 |

The results show an average of the values obtained along 48–72 hours of cultivation.

EXAMPLE 3

The culture medium presents as its source of Nitrogen 1.5% of tryptone and 1% of yeast extract. As a source of Carbon, different concentrations of xylose and xylans. The mineral salts of this culture medium are the ones described above, (Tables II and III).

The culture conditions were:
pH = 7.2
Temperature = 34° C.
Agitation = 750 r.p.m.
17 hours after inoculating the fermenter, the culture was put in continuous.

TABLE VIII

| Composition of medium | | Dilution | | $\mu$/100 culture |
|---|---|---|---|---|
| Xylose | Xylans | Speed | pH | medium |
| 0.5 | 0.5 | 0.1 | 7.2 | 107 |
| 0.2 | 0.8 | 0.1 | 7.2 | 186 |

TABLE VIII-continued

| Composition of medium | | Dilution | | $\mu$/100 culture |
|---|---|---|---|---|
| Xylose | Xylans | Speed | pH | medium |
| 0.2 | 0.8 | 0.2 | 7.2 | 110 |
| 0.1 | 0.9 | 0.1 | 7.2 | 177 |
| — | 1 | 0.1 | 7.2 | 128 |

We claim:
1. Process for producing glucose-isomerase, which comprises culturing continuously or discontinuously, under aerobic conditions, a strain of the species *Streptomyces griseoflavus* A-40 (NCIB-11542) in a culture medium and recovering glucose-isomerase from said medium.

2. Process for producing glucose-isomerase, as claimed in claim 1 wherein the culture medium has the following composition: soy flour of a concentration ranging from 0.1% to 10%, and/or tryptone of a concentration ranging from 0.01% to 2%, and/or xylans of a concentration ranging from 0.1% to 2%, and further containing an ammonium salt.

3. Process for producing glucose isomerase according to claim 2 wherein said ammonium salt is ammonium sulphate.

4. Process for obtaining glucose-isomerase as claimed in claim 1 wherein the cultivation takes place at a temperature ranging between 20° C. and 50° C., and wherein the pH ranges between 3 and 10.

5. Process for producing glucose-isomerase according to claim 4 wherein said temperature is between 30° C. and 35° C. and said pH is between 6.5 and 7.5.

6. Process for producing glucose-isomerase as claimed in claim 1 wherein the culture is subjected to agitation at between 50 and 1000 r.p.m.

7. Process for producing glucose-isomerase, as claimed in claim 1 wherein the microorganism has a speed of dilution in continuous culture that ranges between 0.05 and 1.2 hours$^{-1}$.

8. The process for producing glucose-isomerase according to claim 1 wherein the cultivation time ranges between 17 and 215 hours and the units/gram of cells produced is between 107 and 1000.

9. The process for producing glucose-isomerase according to claim 9 wherein the cells of said strain are separated from the culture medium and are washed with a buffer comprising imidazole at a concentration of $5 \times 10^{-2}$ molar, hexahydrated cobalt chloride at a concentration of between $10^{-3}$ and $10^{-4}$ molar and heptahydrated magnesium sulphate at a concentration between $10^{-3}$ and $10^{-2}$ molar and at a pH between 6 and 7.5.

10. The process for producing glucose-isomerase according to any one of claims 1 or 9 wherein cells of said strain in the form of a cellular suspension are admixed with a medium for isomerization comprising up to 45% fructose, heptahydrated magnesium sulphate at between $5 \times 10^{-5}$ and $10^{-2}$ molar, hexahydrated cobalt chloride at a concentration between $5 \times 10^{-5}$ and $10^{-3}$ molar and imidazole at $5 \times 10^{-2}$ molar, the pH of isomerization being between 6 and 8.5 and the temperature of reaction being between 50° and 90° C.

11. The process according to claim 10 wherein said pH is between 7 and 7.8 and said temperature of reaction is between 60° and 70° C.

* * * * *